(12) United States Patent
Muramatsu

(10) Patent No.: US 6,691,586 B2
(45) Date of Patent: Feb. 17, 2004

(54) MICRO ACTUATOR

(75) Inventor: Naoki Muramatsu, Tokyo (JP)

(73) Assignee: Mitsubishi Denki Kabushiki Kaisha, Tokyo (JP)

(*) Notice: Subject to any disclaimer, the term of this patent is extended or adjusted under 35 U.S.C. 154(b) by 0 days.

(21) Appl. No.: 09/581,616

(22) PCT Filed: Dec. 15, 1997

(86) PCT No.: PCT/JP97/04601
§ 371 (c)(1), (2), (4) Date: Jun. 15, 2000

(87) PCT Pub. No.: WO99/30877
PCT Pub. Date: Jun. 24, 1999

(65) Prior Publication Data
US 2003/0110874 A1 Jun. 19, 2003

(51) Int. Cl.[7] ............................................. A61B 17/28
(52) U.S. Cl. .................. 74/25; 74/89.23; 294/100; 901/38; 901/39
(58) Field of Search ............... 74/25, 89.23, 89.28; 294/100; 901/38, 39

(56) References Cited

U.S. PATENT DOCUMENTS

| | | | | |
|---|---|---|---|---|
| 714,989 A | * | 12/1902 | Worthington | 294/100 X |
| 3,202,449 A | * | 8/1965 | Lemelson | 294/100 X |
| 3,927,424 A | * | 12/1975 | Itoh | 294/100 X |
| 4,828,309 A | * | 5/1989 | Germaine | 294/100 |
| 5,332,275 A | * | 7/1994 | Conway et al. | 294/100 |
| 5,339,803 A | * | 8/1994 | Mayzels et al. | 128/20 |
| 5,458,387 A | * | 10/1995 | Conway et al. | 294/100 |
| 5,895,084 A | * | 4/1999 | Mauro | 901/38 |
| 5,964,780 A | * | 10/1999 | Balazs | 901/39 |

FOREIGN PATENT DOCUMENTS

| | | | |
|---|---|---|---|
| EP | 0467873 | 1/1992 | |
| JP | 61-112889 | 7/1986 | |
| JP | 5-111883 | 5/1993 | ............... B25J/7/00 |
| JP | 5-293778 | 11/1993 | |
| JP | 8-90477 | 4/1996 | ............... B25J/15/08 |
| JP | 8-198578 | * 8/1996 | |
| JP | 9-11175 | * 1/1997 | |
| JP | 10-329077 | * 12/1998 | |
| JP | 11-38014 | * 2/1999 | |
| JP | 11-320472 | * 11/1999 | |

OTHER PUBLICATIONS

96–DETC/ DAC–1497 (Proceedings of the 1996 ASME Design Engineering Technical Conference, Aug. 18–22, 1996, Irvine, California), which is rewritten in English.
International Search Report.

* cited by examiner

Primary Examiner—David A. Bucci
Assistant Examiner—Colby Hansen
(74) Attorney, Agent, or Firm—Sughrue Mion, PLLC

(57) ABSTRACT

A micro actuator including: a translationally driving section having a moving portion which is incorporated in a case 14 and moves translationally; and a displacement enlarging member 1 having one end portion 1g connected to the moving portion of the translationally driving section and another end portion 1h connected to the case, wherein as the one end portion 1g is pulled on the basis of the translational movement, the amount of displacement of its distal end 1a is enlarged.

13 Claims, 9 Drawing Sheets

AMOUNT OF DISPLACEMENT OF DISTAL END PORTION

AMOUNT OF DISPLACEMENT OF DISTAL END PORTION

MICRO ACTUATOR

TECHNICAL FIELD

The present invention relates to a micro actuator, and more particularly to improvements in a micro actuator in which the amount of translational displacement can be easily enlarged.

BACKGROUND ART

There are many micro actuators (hereinafter referred to as actuators) which are in a research-and-development stage, but the number of actuators which have reached the product stage is very small. This is conceivably due partly to the difficulty in the microminiturization of the actuators themselves. In such a situation, Japanese Patent Unexamined Publication No. Hei. 8-90477 is known as the conventional art of the actuator which discloses the basic configuration of a product.

Such an actuator is characterized by a drive mechanism in which the expanding and contracting displacement of a movable frame due to a piezoelectric element is converted to the opening and closing displacement of a U-shaped pair of gripper fingers through a swinging mechanism consisting of a hinge and levers, and there is an advantage in that the pair of gripper fingers exhibits equalized opening and closing behavior with respect to an object to be gripped.

With the above-described conventional actuator, however, to utilize the expanding and contracting displacement of the piezoelectric element as the displacement for actuating the gripper, a mechanism for enlarging the displacement must be provided, so that the structure has been complex. For example, since the expanding and contracting displacement of the piezoelectric element is on the order of nanometers, there has been a problem in that a mechanism for enlargement by a factor of several hundreds is required to obtain an opening and closing displacement of even several hundred microns for the gripper fingers.

DISCLOSURE OF THE INVENTION

The invention has been made to overcome the above-described problems, and its object is to provide an actuator in which the amount of displacement of a distal end portion gets large on the basis of a slight amount of displacement of a driving section without using an enlarging mechanism.

To attain this object, the actuator according to a first aspect is characterized by comprising: a translationally driving section having a moving portion which is incorporated in a case and moves translationally; and a displacement enlarging member having one end portion connected to the moving portion of the translationally driving section and another end portion connected to the case, wherein as the one end portion is pulled on the basis of the translational movement, the displacement enlarging member is extended from the end portion and the one end portion more than an amount of the translational movement, and an amount of displacement of its common distal end is enlarged.

The actuator according to a second aspect is characterized by comprising: a translationally driving section having a moving portion which is incorporated in a case and moves translationally; and a displacement enlarging member including a common portion having a distal end in common, at least two side portions extending from the common portion and opposing each other, and an open portion which is located on a side away from the common portion and is open, wherein one end of the open portion is connected to the translationally driving section, another end of the open portion is connected to the case, and the distal end is subjected to enlarging displacement on the basis of the translational displacement of the translationally driving section.

The actuator according to a third aspect is characterized in that the displacement enlarging member exhibits a buckling phenomenon as the one end of the open portion is translationally displaced.

The actuator according to a fourth aspect is characterized in that the common portion of the displacement enlarging member has a secured portion in which distal end portions of the displacement enlarging member are secured together in a superposed manner.

The actuator according to a fifth aspect is characterized in that first and second displacement enlarging members are provided, and one ends of the open portions of the first and second displacement enlarging members are held in common and are connected to the translationally driving section.

The actuator according to a sixth aspect is characterized in that the shape of the displacement enlarging member is substantially V-shaped.

The actuator according to a seventh aspect is characterized in that a projecting portion which projects to an outside is provided on at least one of the side portions of the displacement enlarging member.

The actuator according to an eighth aspect is characterized in that, instead of the common portion having the distal end of the displacement enlarging member in common, the common portion is one having a vicinity of the distal end and a central portion of the displacement enlarging member in common.

The actuator according to a ninth aspect is characterized in that the translationally driving section is comprised of a motor having a shaft and a converting section for converting the rotation of the shaft to translational displacement, and wherein there are provided a connecting section for connecting together the converting section and one end of the displacement enlarging member, and a fixing section provided in the case for fixing another end of the displacement enlarging member, the connecting section being also accommodated in the case.

The actuator according to a 10th aspect is characterized in that the converting section is comprised of a nut with an internal thread formed therein and a transmitting member threadedly engaged with the nut and connected to the shaft, and wherein the length of threaded portions of the nut, the shaft or the nut, and the transmitting member is less than or equal to a maximum value of the amount of translational displacement.

The actuator according to an 11th aspect is characterized in that a substantially circularly formed circular portion is provided at one end portion of the open portion of the displacement enlarging member, and a groove with which the circular portion is engaged is provided in the connecting section.

The actuator according to a 12th aspect is characterized in that the nut has the shape of a substantially quadrangular prism, and a guide portion for guiding the nut as an outer surface of the nut is slidingly engaged therewith has opposite ends which are substantially semicircular.

BEST MODE FOR CARRYING OUT THE INVENTION

Next, a description will be given hereafter of the embodiments of the invention.

First Embodiment

Figure 1A:
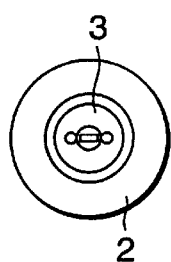
FIG. 1 is cross-sectional views and a side elevational view illustrating an overall actuator according to an embodiment of the invention, in which the part (a) is a side elevational view, the part (b) is a cross-sectional view, and the part (c) is a cross-sectional view taken in the direction of arrows along line C—C in the part (b)
Figure 1B:
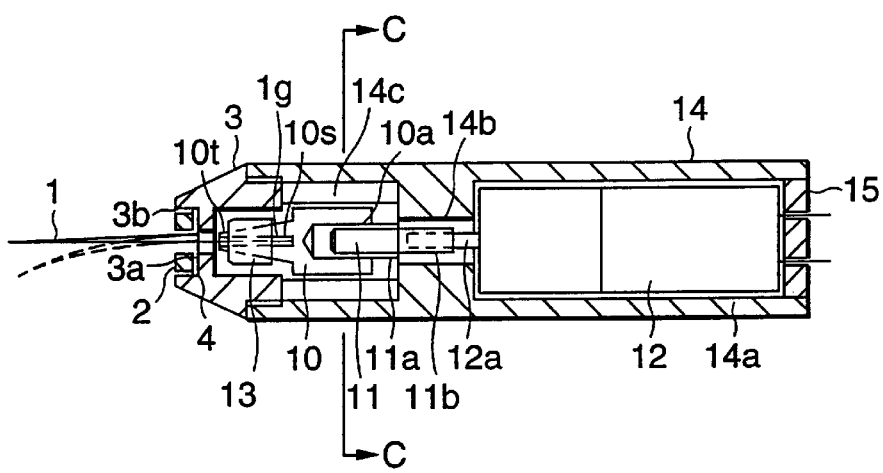
Figure 1C:
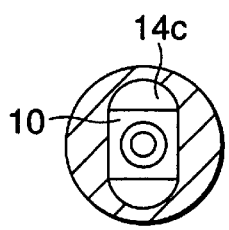
Figure 2:
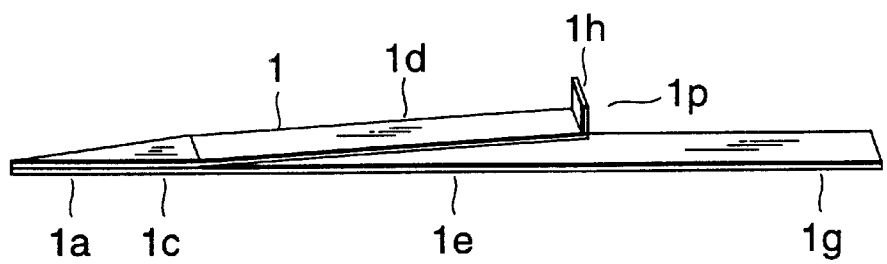
FIG. 2 is a perspective view illustrating an operating finger shown in FIG. 1.

Referring to FIGS. 1 and 2, a description will be given of an embodiment of the invention. FIG. 1 is cross-sectional views and a side elevational view of an actuator, and FIG. 2 is a perspective view of a plate-shaped displacement enlarging member.

In FIGS. 1 and 2, the actuator is comprised of an operating finger 1 serving as a substantially V-shaped displacement enlarging member whose distal end portion undergoes enlarging displacement on the basis of translational displacement so as to operate on a very small object; a drive section for imparting a driving force on the operating finger 1 by rotating; a converting section for converting the rotation of this drive section to translational movement; a connecting section for connecting this converting section and the operating finger 1; a case section for accommodating the converting section, the drive section, and the connecting section; and a fixing section for fixing a portion of the operating finger 1 by making use of the case section.

As shown in FIG. 2, the operating finger 1 includes a common portion 1a which is beam-like and plate-shaped and has distal ends in common in a superposed manner; two side portions 1d and 1e extending from this common portion 1a and opposing each other; an open portion 1p which is located on the side away from the common portion 1a and is open; one end 1g of the open portion; and a hook-like leg 1h thereof. It should be noted that the common portion (distal end portion) 1a of the operating finger 1 acts on the object.

Here, a metallic material having a spring characteristic is used for the operating finger 1, and a secured portion 1c, in which the side portion 1d and the side portion 1e are secured together by means of soldering, welding, an adhesive agent, or the like, is formed in the common portion 1a. It should be noted that, instead of the metallic material, a nonmetallic material such as a resin may be used depending on the object.

The drive section is, for example, a coreless dc motor (hereafter referred to as motor) 12 with a reducing gear having a rotor shaft 12a which is connected to the end 1g of the operating finger 1 through the converting section so as to cause the end 1g to undergo translational displacement.

The converting section includes a threaded shaft 11 having a thread 11a on its outer periphery and having a hollow portion 11b in which the rotor shaft 12a of the motor 12 is fitted and fixed, as well as a nut 10 having a thread 10a on a peripheral surface of a hollow portion formed by cutting its rear end, the thread 11a of the threaded shaft 11 being threadedly engaged with the thread 10a. The converting section is arranged in such a manner as to convert the rotation of the rotor shaft 12a of the motor 12 to translational displacement of the nut 10. As shown in FIGS. 1(b and c), the nut may have the shape of a quadrangular prism.

The connecting section includes a substantially conically shaped conical portion in which a tapered screw 10t is formed on an outer peripheral portion of a distal-end projection of the nut 10, as well as a tapered nut 13 for being threadedly engaged with the tapered screw 10t. A slit 10s is provided in the center of the conical portion of the nut 10, the end 1g of the operating finger 1 is inserted in this slit 10s, and the tapered nut 13 is threadedly engaged with the tapered screw 10t, thereby connecting and fixing the end 1g of the operating finger 1.

The case section is formed by a case 14, a cover 15 for closing a right-hand end face of the case 14, and a cap 3 which is engaged with and fixed to a left-hand end face of the case 14.

The case 14 includes a motor accommodating portion 14a formed in a hollow cylindrical shape for accommodating the motor 12 in its cylindrical space portion, a threaded-shaft accommodating portion 14b for accommodating the rotor shaft 12a of the motor 12 and a portion of the threaded shaft 11, and a nut accommodating portion 14c for accommodating the nut 10 and serving as a guide portion formed such that its entire portion is oval and its end portions are substantially semicircular, as shown in the C—C cross-sectional view of FIG. 1.

The cap 3 has a hollow cylinder in which the connecting section is contained and which has a tubular shape with a cross section formed in a substantially trapezoidal shape and has a two-staged through hole in its center. A flange 3a is provided such that an end face of this hollow cylinder is formed in a recessed shape, and a thread 3b is provided on the peripheral surface of the recessed portion.

The fixing section fixes the leg 1h of the operating finger 1 to the cap 3 as the leg 1h of the operating finger 1 abuts against the flange 3a of the cap 3 with a washer 4 interposed therebetween and a thread formed on the outer peripheral surface of a holder 2 is threadedly engaged with the thread 3b of the recessed portion of the cap 3.

In the above-described configuration of the actuator, a description will be given hereafter of the enlargement and displacement of the distal end of the operating finger 1 on the basis of the rotational displacement of the rotor shaft 12a of the motor 12. Consideration will be given by using a model in which, as shown in FIG. 3, the end of the operating finger 1 is pulled by a load P with the hook-like leg 1h of the operating finger 1 fixed (at the point 0 in FIG. 3) on X and Y axes.

Figure 3:
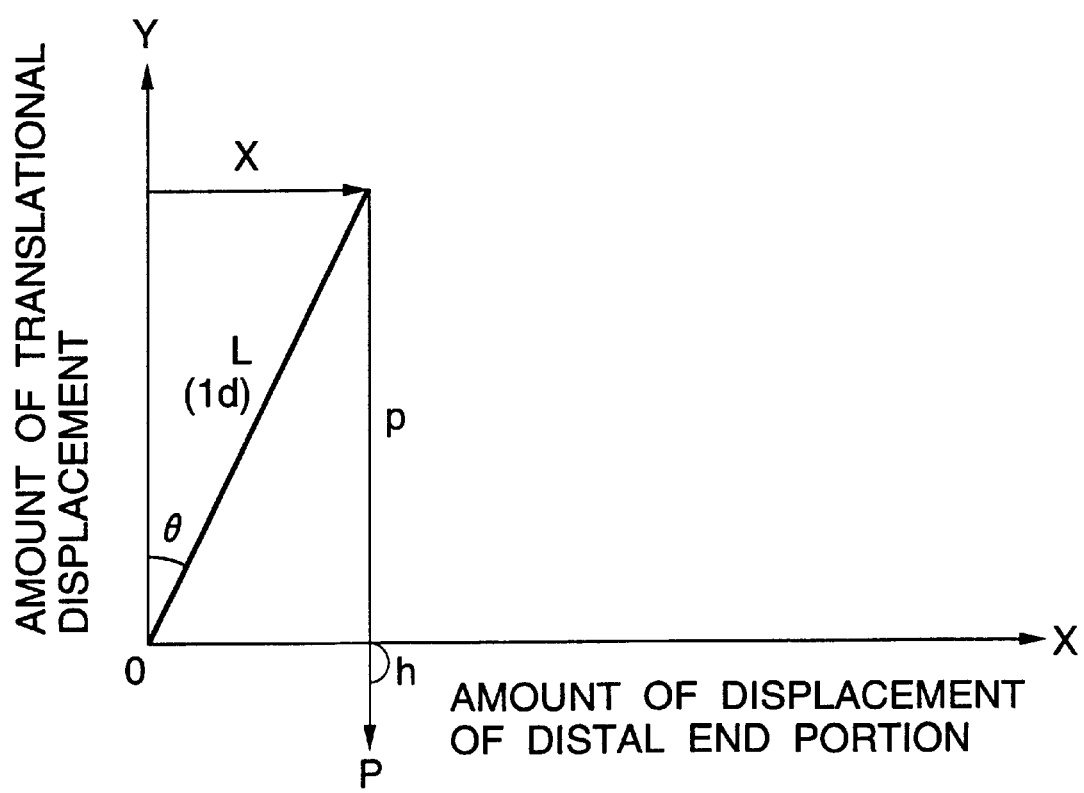
FIG. 3 is a model diagram explaining the amount of displacement of a distal end portion of the operating finger shown in FIG. 1.

In FIG. 3, if the rate of displacement, X, in the X-axis direction of the operating finger 1 with respect to a slight amount of translational displacement, h, in the X-axis direction of the end of the operating finger 1 (hereafter, the rate of this displacement will be referred to as the amount of displacement of the distal end portion) is assumed to be an enlargement rate G=X/h, the amount of displacement, X, of the distal end portion, the amount of translational displacement, h, and the enlargement rate G can be expressed by formulae shown below. Incidentally, it is assumed that the beam L does not bend and that $\Theta$ is infinitesimal.

$$X = L\sin\Theta \approx L\Theta$$

$$h = L(1-\cos\Theta) \approx L(\Theta^2/2)$$

$$G = X/h = 2/\Theta$$

Specifically, if it is assumed that the amount of translational displacement, h, of the operating finger 1 is 0 to 10° in terms of the angle $\Theta$, the enlargement rate G becomes $\infty$ to 11.5. Namely, the amount of displacement, X, of the distal end portion is enlarged with respect to a slight amount of translational displacement, h.

For example, as a result of an experiment conducted by using as the operating finger 1 a phosphor bronze sheet for a spring having a thickness of 0.1 mm, a width of 2 mm, and a length of 30 mm, the amount of displacement, X, of the distal end portion was X=8.5 mm with respect to an amount of translational displacement, h, of 1 mm, and the tensile force P for forced displacement was 60 g or thereabouts.

In addition, to make the apparatus more compact, it is possible to make use of a buckling phenomenon, for example. The buckling phenomenon referred to herein means the phenomenon in which when an applied load reaches a certain value, transverse displacement quickly occurs. Namely, by causing the end of the operating finger 1 to be translationally displaced, the distal end portion of the operating finger 1 is quickly displaced.

To obtain such a buckling phenomenon, the hook-like leg 1h of the operating finger 1 and the other leg 1g thereof are arranged to be disposed in very close proximity to each other. That is, as described above, since the leg 1h of the operating finger 1 is held onto the flange 3a with the washer 4 interposed therebetween by means of the holder 2, it suffices if the amount of the tightening allowance of the leg 1h is adjusted so as to obtain the buckling phenomenon.

Figure 4:
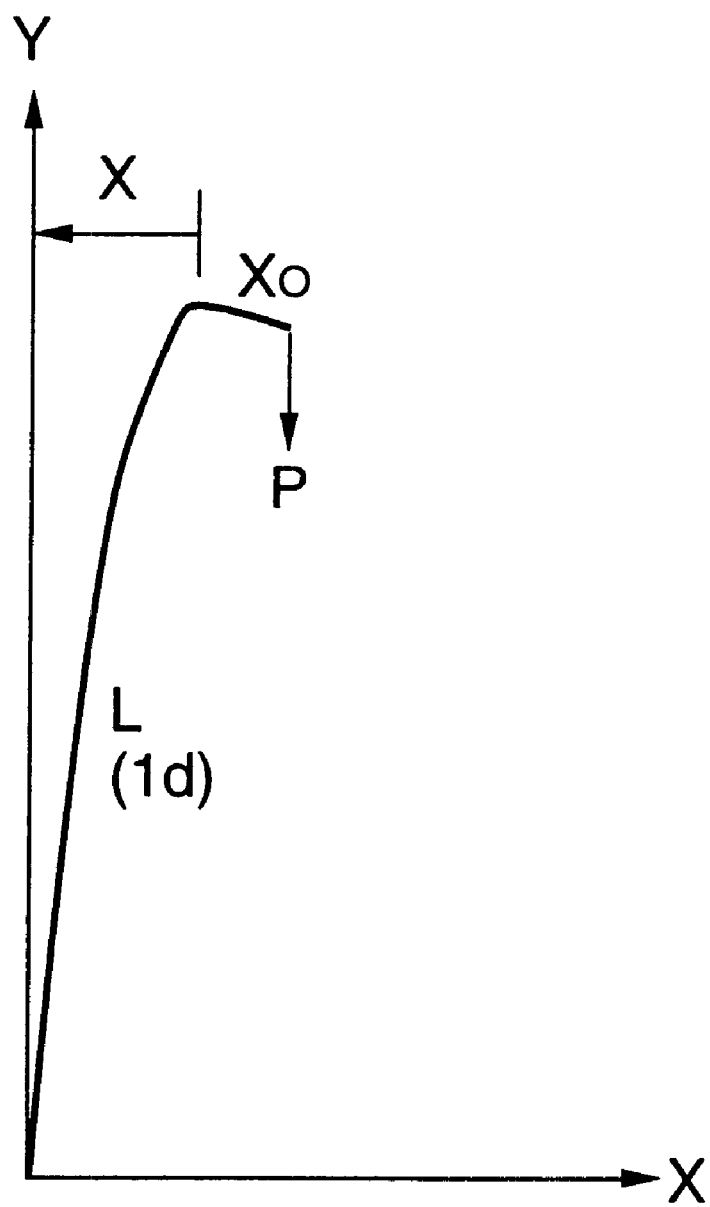
FIG. 4 is a model diagram in which the distal end portion of the operating finger shown in FIG. 3 is enlarged.

In such a configuration, from FIG. 4 which makes clearer the distal end portion of the model shown in FIG. 3, the relation between the load P and the amount of displacement, X, of the distal end portion is expressed by the formula shown below. It should be noted, however, that $X_0$ is the amount of eccentric displacement of the load P.

$$P = (EI/L^2)\{\cos^{-1}(X_0/(X+Y_0))\}^2 \quad (1)$$

where E is the modulus of longitudinal elasticity (kg/mm²), and I is the moment of inertia of area (mm²).

Here, if it is assumed that $X_0 \approx 0$, we have $$\cos^{-1}X_0/(X+X_0) \approx \pi/2$$

Figure 5:
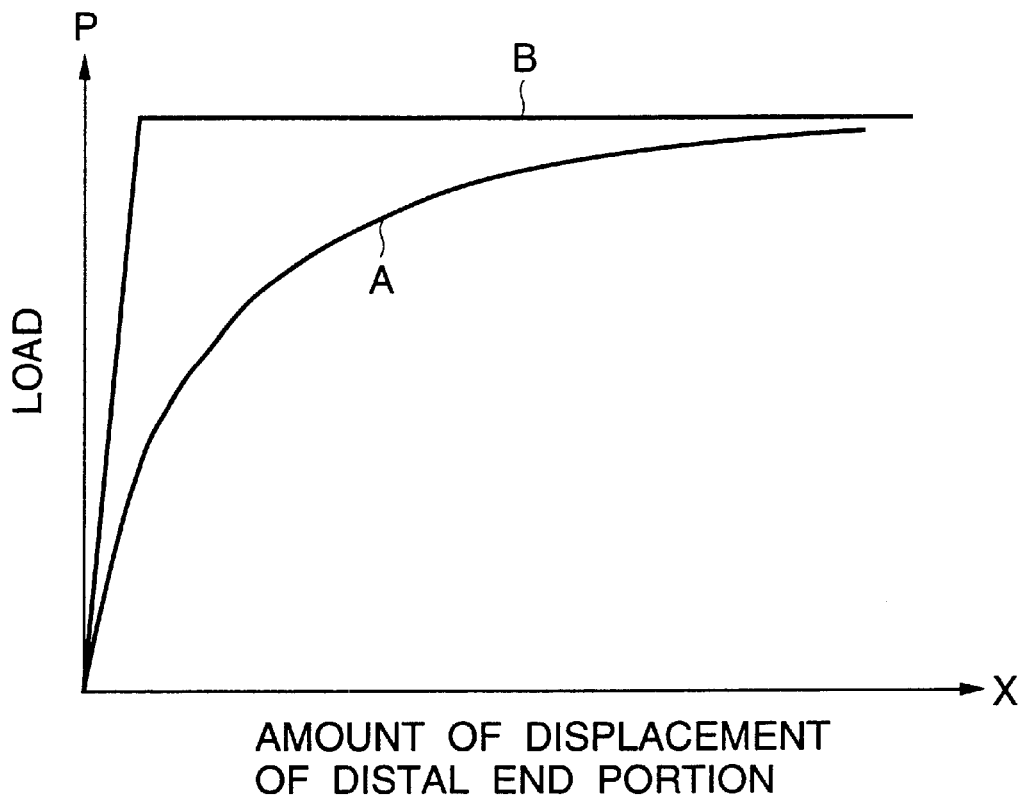
FIG. 5 is a graph illustrating the load on the operating finger and the amount of displacement of the distal end portion in FIG. 1.

As a result, the load P becomes fixed at $(EI^2\pi)/(4L^2)$ irrespective of the amount of displacement, $X_0$, as shown by a curve B in FIG. 5.

Next, mainly referring to FIG. 1, a description will be given of the operation of the actuator configured as described above. First, a power supply is turned on for the motor 12, and the rotor shaft 12a of the motor 12 rotates. This rotation causes the nut 10 to be translationally displaced in the rightward direction in FIG. 1 through the threaded shaft 11. This translational displacement is transmitted to the nut 10 through the threaded shaft 11, and the nut 10 slides in the nut accommodating portion 14c and is displaced in the rightward direction in FIG. 1 with respect to the axis of the threaded shaft 11.

Concurrently, the end 1g of the operating finger 1 is forcefully displaced with the same amount of displacement and in the same direction (in the direction in which it is pulled by the rotor shaft 12a of the motor 12), and bending moment is applied to the operating finger 1, so that the operating finger 1 is bent from the direction indicated by the solid line toward the direction indicated by the broken line, as shown in FIG. 1. Here, if the operating finger 1 has a normal bending characteristic, the operating finger 1 exhibits the displacement characteristic such as the one shown by a curve A in FIG. 5, but if the operating finger 1 is arranged to display a buckling phenomenon, the operating finger 1 exhibits the displacement characteristic such as the one shown by the curve B in FIG. 5. This enlarging/bending displacement is made to act on the object.

On the other hand, if the rotation of the rotor shaft 12a of the motor 12 is reversed, the rotation causes the nut 10 to be translationally displaced in the leftward direction in FIG. 1 through the threaded shaft 11. This translational displacement is transmitted to the nut 10 through the threaded shaft 11, and the nut 10 is displaced in the nut accommodating portion 14c in the axial direction. As this translational displacement is transmitted in the same way as described above and causes the bending displacement of the operating finger 1 to be canceled, and the distal end portion of the operating finger 1 is returned as indicated by the solid lines in FIG. 1.

In addition, although not shown, the common portion 1a of the operating finger 1 in FIG. 2 may be located away from the distal end. According to such a configuration, since the common portion 1a ceases to be present at the distal end of the operating finger 1, the thickness of the distal end of the operating finger 1 can be made thin, and the amount of enlarging displacement can be easily adjusted by the position where the common portion 1a is formed.

It should be noted that, as for the converting section, the rotor shaft 12a of the motor 12 where the thread is formed may be directly threadedly engaged with the nut 10. In addition, although the leg 1h of the operating finger 1 is fixed to the cap 3, the leg 1h of the operating finger 1 may not be necessarily fixed to the cap 3, and it suffices if it is fixed to the vicinity of the end 1g of the operating finger 1. Furthermore, the secured portion 1c of the operating finger 1 is not necessarily required in the light of the repeated strength and the like.

Second Embodiment

Figure 6:
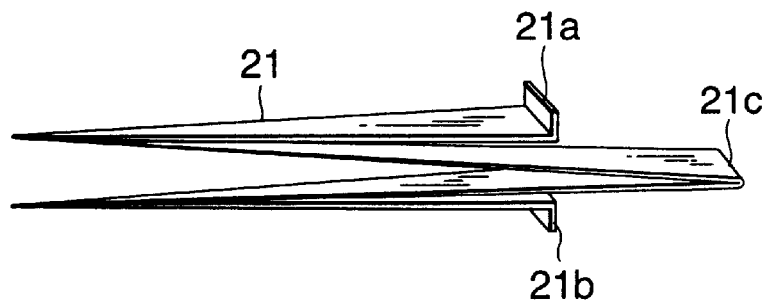
FIG. 6 is a perspective view illustrating a pair of gripper fingers of the actuator according to another embodiment of the invention.
Figure 7:
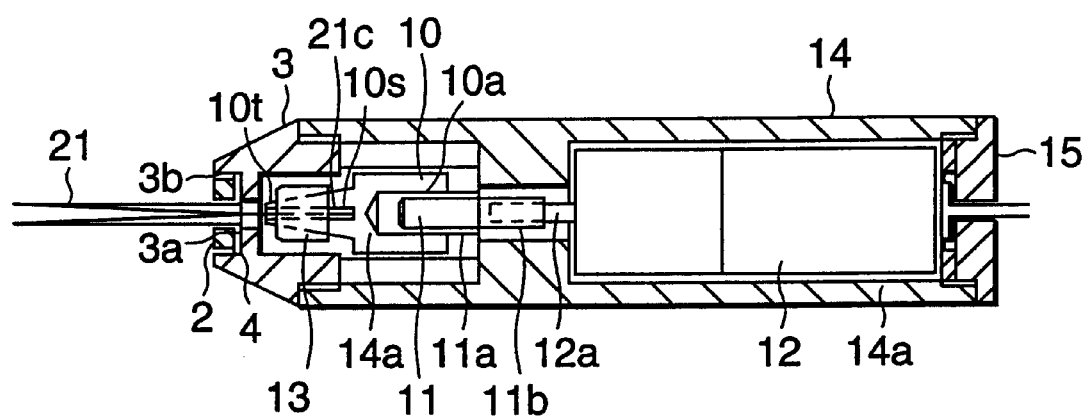
FIG. 7 is a cross-sectional view illustrating the overall gripper fingers shown in FIG. 6.

Referring to FIGS. 6 and 7, a description will be given of another embodiment of the invention. FIG. 6 is a perspective view of the displacement enlarging member having a nipping portion, and FIG. 7 is a cross-sectional view of the actuator having the nipping portion. In the drawings, the same reference numerals as those of FIG. 1 denote identical or corresponding portions, and a description thereof will be omitted.

In FIGS. 6 and 7, this actuator differs from that of FIG. 1 only in the displacement enlarging member, the connecting section, and the fixing section, so that a description will be given of such arrangements. First, a pair of gripper fingers 21 serving as the displacement enlarging member is made of a beam-like member formed substantially in an M-shape and having a spring characteristic. The pair of gripper fingers 21 is formed just as if the ends 1g of two operating fingers 1, one being shown in FIG. 2, are integrated in common, an apex portion 21c is provided in common, and hook-like legs 21a and 21b are respectively provided at ends of the open portions.

The connecting section is arranged such that the apex portion 21c of the gripper fingers 21 is inserted into the slit 10s of the nut 10, and the tapered nut 13 is threadedly engaged with the tapered screw 10t, thereby joining and fixing the apex portion 21c of the gripper fingers 21.

The fixing section is arranged such that the legs 21a and 21b of the gripper fingers 21 are made to abut against the flange 3a of the cap 3 with the washer 4 interposed therebetween, and the thread formed on the outer peripheral surface of the holder 2 is threadedly engaged with the thread 3b of the recessed portion of the cap 3, thereby fixing the legs 21a and 21b of the gripper fingers 21 to the cap 3.

Referring to FIG. 7, a description will be given of the operation of the actuator configured as described above. First, if the power supply is turned on for the motor 12, the rotor shaft 12a of the motor 12 rotates, and this rotation is transmitted to the nut 10 through the threaded shaft 11, causing the nut 10 to be displaced inside the nut accommodating portion 14c in the rightward direction in FIG. 1 with respect to the threaded shaft 11.

Concurrently, the apex portion 21c of the gripper fingers 21 is forcefully displaced with the same amount of displacement and in the same direction, and bending moment is applied to the gripper fingers 21, so that its distal end portions are bent in mutually approaching directions and are closed to grip the object.

Meanwhile, if the rotation of the motor 12 is reversed, the rotation causes the nut 10 to be translationally displaced in the opposite direction through the threaded shaft 11. This translational displacement is transmitted in the same way as described above and causes the apex portion 21c of the gripper fingers 21 to be translationally displaced, thereby causing the distal end portions of the operating fingers 21 to release the gripping of the object.

Figure 8A:
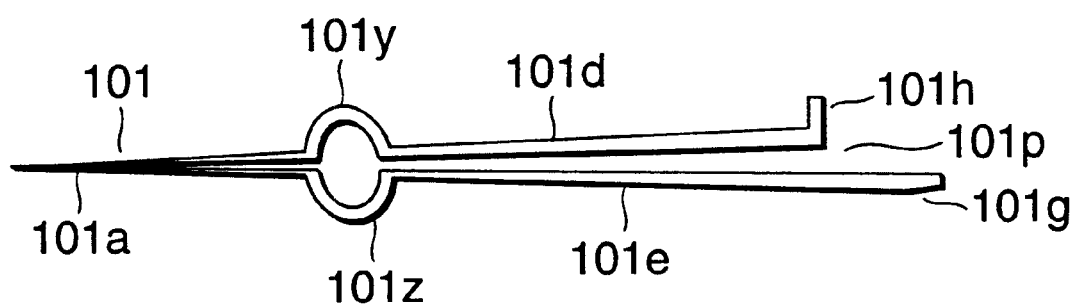
FIG. 8 is a perspective view of the operating finger and the pair of gripper fingers according to the other embodiment of the invention.
Figure 8B:
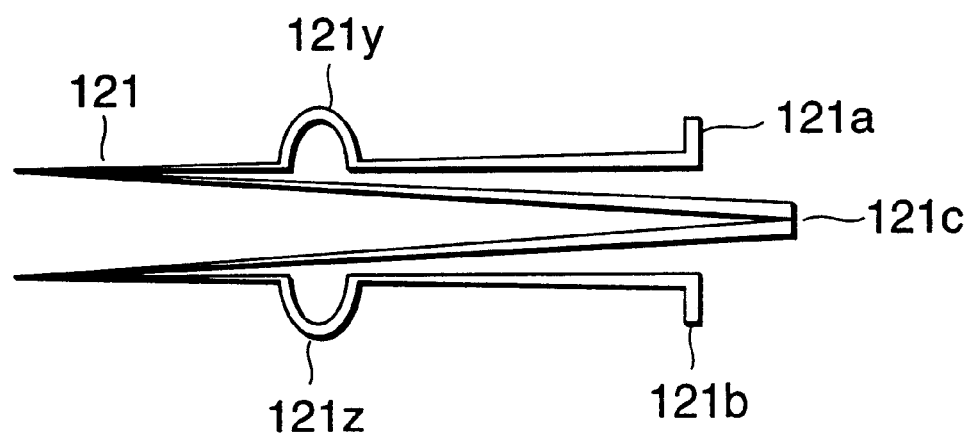

In addition, as shown in FIG. 8, an arrangement may be provided such that semicircular projecting portions 110y and 101z or 121y and 121z which project to the outer sides are provided on side portions of an operating finger 101 and a pair of gripper fingers 121, respectively. According to such an arrangement, the aforementioned enlargement rate G can be varied by the projecting portion 101y and the like, so that a desired displacement of the distal end portion can be easily realized. It should be noted that the kind of shape is not particularly limited and may be a substantially triangular shape, a semielliptical shape, and a semioval shape, and either one of the projecting portions 101y and 101z may be used.

Figure 9A:
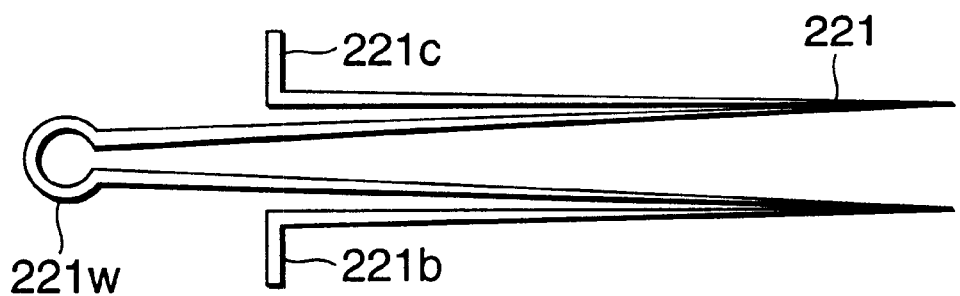
FIG. 9 is a perspective view of the operating finger and the pair of gripper fingers according to the other embodiment of the invention.
Figure 9B:
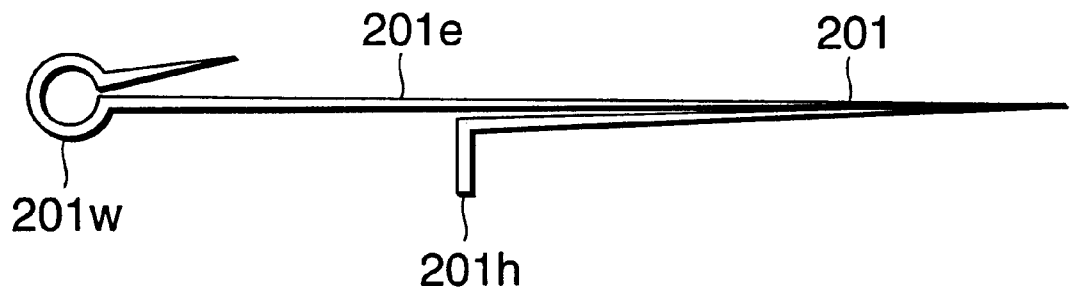
Figure 10:
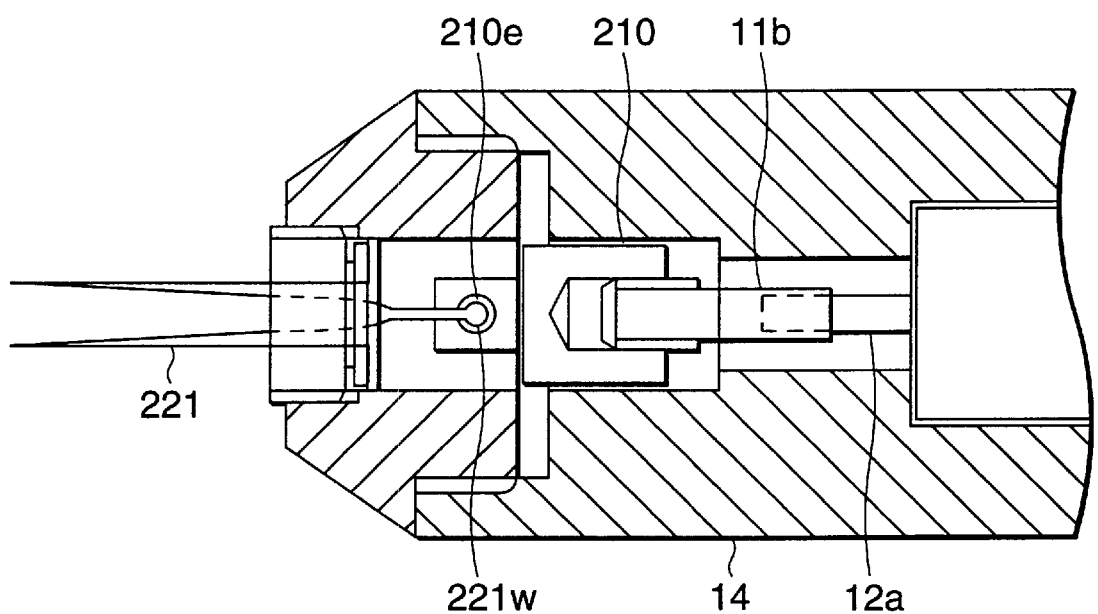
FIG. 10 is a cross-sectional view in which the pair of gripper fingers shown in FIG. 9 is engaged in a connecting section.

In addition, as shown in FIGS. 9 and 10, an arrangement may be provided such that circular portions 201w and 221w, which are formed in substantially circular shapes, are provided on end portions of an operating finger 201 and a pair of gripper fingers 221, respectively, while a groove 210e to which this circular portion is engaged is provided in a nut 210. According to such an arrangement, the circular portions 201w and 221w of the operating finger 201 and the gripper fingers 221 can be easily engaged and fixed in the groove 210e of the nut 210 or can be removed therefrom.

Third Embodiment

Figure 11:
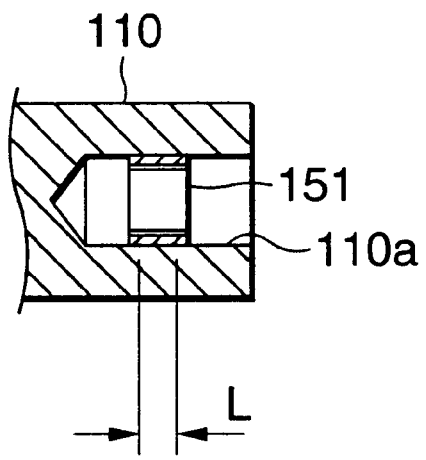
FIG. 11 is a cross-sectional view of a nut of a converting section according to still another embodiment of the invention.
Figure 12:
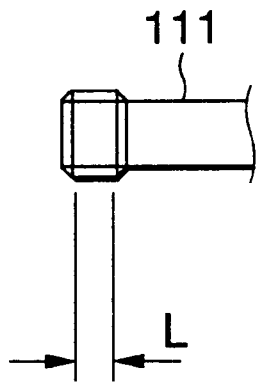
FIG. 12 is a cross-sectional view illustrating a threaded shaft of the converting section according to the still other embodiment of the invention.

Referring to FIGS. 11 and 12, a description will be given of still another embodiment of the invention. FIG. 11 is a cross-sectional view of the nut, and FIG. 12 is a perspective view of the threaded shaft which is threadedly engaged with the nut shown in FIG. 11. In this actuator, only the nut 10 and the threaded shaft 11 shown in FIG. 1 are different, and a translational-displacement-amount limiting portion is provided to limit the amount of the translational displacement of the operating (gripper) finger(s).

In FIGS. 11 and 12, the translational-displacement-amount limiting portion consists of a nut 110 and a threaded shaft 111 serving as a transmitting member which is threadedly engaged with the nut 110. The nut 110 has in its cut hollow portion 110a of a substantially cylindrical shape a limiting nut 151 which is engaged and fixed therein for limiting the translational movement. The limiting nut 151 with an internal thread formed therein as well as the threaded shaft 111 are formed with effective thread length L, and this effective thread length L substantially agrees with a maximum value of the amount of the translational displacement of the finger.

Referring to FIGS. 1, 11, and 12, a description will be given of the operation of the actuator configured as described above. If the motor 12 is driven in the same way as the first embodiment and the threaded shaft 111 is driven by a predetermined number of revolutions or more, the limiting nut 151 is disengaged from the threaded shaft 111 and idles, so that the nut 110 is not translationally displaced any further. Namely, as the threaded shaft 111 is rotated forwardly or reversely, the operating finger 1 is driven only within the amount of translational displacement of the effective thread length L.

It should be noted that although, in the above-described embodiment, the limiting nut 151 is threadedly engaged with the threaded shaft 111, an arrangement may be provided such that the rotor shaft 12a of the motor 12 is elongated and a thread is formed on its outer periphery, and the limiting nut 151 and the rotor shaft 12a may be threadedly engaged with each other.

As described above, according to a first aspect of the invention, since the amount of displacement of the distal end portion of the displacement enlarging member becomes large on the basis of a slight amount of translational displacement, there is an advantage in that a simple mechanism can be used without requiring an enlarging mechanism.

According to a second aspect of the invention, since the amount of displacement of the distal end portion of the displacement enlarging member becomes large on the basis of a slight amount of translational displacement, there is an advantage in that a simple mechanism can be used without requiring the enlarging mechanism.

According to a third aspect of the invention, in addition to the advantage of the second aspect of the invention, there is an advantage in that, in particular, the diameter of the distal end portion of the actuator can be made small since the displacement enlarging member exhibits a buckling phenomenon as the one end of the open portion is translationally displaced.

According to a fourth aspect of the invention, in addition to the advantage of the second aspect of the invention, there is an advantage in that the displacement enlarging member has high strength against the repeated operation of the bending of the distal end since the rigidity of the common portion of the displacement enlarging member increases.

According to a fifth aspect of the invention, in addition to the advantage of the second aspect of the invention, there is an advantage in that an object can be gripped or released by a simple mechanism without requiring the enlarging mechanism since the distal end portions of the first and second displacement enlarging members are both bent inwardly on the basis of a slight amount of translational displacement, and since the amount of this displacement is large.

According to a sixth aspect of the invention, in addition to the advantage of the second aspect of the invention, there is an advantage in that the processing of the displacement enlarging member is facilitated.

According to a seventh aspect of the invention, in addition to the advantage of the second aspect of the invention, there is an advantage in that the amount of enlarging displacement can be easily adjusted by such as the size and the shape of the projecting portion of the displacement enlarging member.

According to an eighth aspect of the invention, in addition to the advantage of the second aspect of the invention, since the common portion ceases to be present at the distal end of the displacement enlarging member, there are advantages in that the thickness of the distal end of the displacement enlarging member can be made small, and that the amount of enlarging displacement in the distal end portion of the displacement enlarging member can be easily adjusted by the position where the common portion is formed.

According to a ninth aspect of the invention, in addition to the advantage of the second aspect of the invention, there are advantages in that the translationally driving section can be formed easily, and that the amount of translational displacement of the translationally driving section can be transmitted to the displacement enlarging member by means of the connecting section.

According to a 10th aspect of the invention, in addition to the advantages of the ninth aspect of the invention, there is an advantage in that the amount of translational displacement can be limited by the length of threaded portions of the nut, the shaft or the nut, and the transmitting member.

According to an 11th aspect of the invention, in addition to the advantages of the ninth aspect of the invention, there is an advantage in that the attachment and detachment of the displacement enlarging member with respect to the connecting section are facilitated.

According to an 12th aspect of the invention, in addition to the advantages of the 10th aspect of the invention, there is an advantage in that the processing of the guide portion for the sliding engagement of the nut is facilitated.

Industrial Applicability

As described above, the micro actuator according to the invention is suitable for use in enlargement of the amount of its translational displacement.

What is claimed is:

1. A micro actuator comprising:

a case;

a translationally driving section having a moving portion mounted on said case for translational movement; and a displacement enlarging member having a first end portion connected to said moving portion of said translationally driving section, a second end portion connected to said case, and flexible side portions respectively extending from said first and said second end portions, said flexible side portions being in direct contact with each other to form a common portion having a distal end, wherein as said first end portion translationally moves together with said moving portion through a first distance, (1) said distal end of said common portion moves through a second distance that is greater than said first distance, and (2) an entire length of said displacement enlarging member extending from said case to said distal end of said common portion is elastically bent.

2. A micro actuator comprising:

a case;

a translationally driving section having a moving portion mounted on said case for translational movement; and a displacement enlarging member including at least two flexible side portions that are in direct contact with each other to form a common portion having a distal end, and an open portion located on a side away from said common portion, wherein (1) a first end of said open portion is connected to said translationally driving section, (2) a second end of said open portion is connected to said case, and (3) said distal end is subjected to enlarging displacement on the basis of the translational movement of said translationally driving section, such that an entire length of each of said at least two side portions extending from said case to said distal end of said common portion is elastically bent.

3. The micro actuator according to claim 2, wherein said displacement enlarging member exhibits a buckling phenomenon as said first end of said open portion is translationally displaced.

4. The micro actuator according to claim 2, wherein said common portion of said displacement enlarging member has a secured portion in which distal end portions of said displacement enlarging member are secured together in a superposed manner.

5. The micro actuator according to claim 2, wherein first and second said displace enlarging members are provided, and first ends of said open portions of said first and second displacement enlarging members are held in common and are connected to said translationally driving section.

6. The micro actuator according to claim 2, wherein the shape of said displacement enlarging member is substantially V-shaped.

7. The micro actuator according to claim 2, wherein a projecting portion which projects to an outside is provided on at least one of the side portions of said displacement enlarging member.

8. The micro actuator according to claim 2, wherein said common portion is provided at a central portion of said displacement enlarging member.

9. The micro actuator according to claim 2, wherein said translationally driving section includes a shaft and said moving portion converts the rotation of said shaft to translational displacement, wherein a connecting section is provided for connecting together said moving portion and said first end of said displacement enlarging member, and a fixing section is provided in said case for fixing said second end of said displacement enlarging member to said case.

10. The micro actuator according to claim 9, wherein said moving portion is comprised of a nut with an internal thread formed therein and a transmitting member threadedly engaged with said nut and connected to said shaft, and wherein a length of threaded portions of one of said nut, said shaft, and said transmitting member is equal to or less than a maximum value of the amount of translational displacement.

11. The micro actuator according to claim 9, wherein a circular portion is provided at said second end portion of said open portion of said displacement enlarging member, and a groove with which said circular portion is engaged is provided in said connecting section.

12. The micro actuator according to claim 10, wherein said nut has the shape of a substantially quadrangular prism, and a guide portion for guiding said nut as an outer surface of said nut is slidingly engaged therewith has opposite ends which are substantially semicircular.

13. The micro actuator according to claim 2, wherein said distal end is displaced a distance that is at least 11.5 times greater than a distance of said translational movement of said translationally driving section.

* * * * *